United States Patent
Zima et al.

(10) Patent No.: US 6,497,644 B2
(45) Date of Patent: Dec. 24, 2002

(54) PROCESS FOR RECYCLING AMIDO-CARBOXYLIC ACID ESTERS INTO AMINO-CARBOXYLIC ACIDS

(75) Inventors: George C. Zima, Kingsport, TN (US); Thomas H. Williams, Falls Branch, TN (US); David M. Hitch, Kingsport, TN (US); Jerry L. Miller, Kingsport, TN (US)

(73) Assignee: Eastman Chemical Company, Kingsport, TN (US)

(*) Notice: Subject to any disclaimer, the term of this patent is extended or adjusted under 35 U.S.C. 154(b) by 32 days.

(21) Appl. No.: 09/871,696

(22) Filed: Jun. 4, 2001

(65) Prior Publication Data
US 2002/0052528 A1 May 2, 2002

Related U.S. Application Data
(60) Provisional application No. 60/208,503, filed on Jun. 2, 2000.

(51) Int. Cl.[7] ............................................. C07C 232/00
(52) U.S. Cl. ........................... 584/69; 584/68; 584/70; 584/177
(58) Field of Search ............................. 589/68, 69, 70, 589/177

(56) References Cited

U.S. PATENT DOCUMENTS 4,634,551 A  1/1987  Burns et al. ............... 252/102

(List continued on next page.)

FOREIGN PATENT DOCUMENTS

| EP | 0 402 339 A1 | 12/1990 |
| EP | 415 472 A1 | 3/1991 |
| EP | 0 484 634 A1 | 5/1992 |
| GB | 2 249 104 A | 4/1992 |
| JP | 58-157760 | 9/1983 |
| JP | 6-179648 | 6/1994 |
| JP | 6-306042 | 11/1994 |
| JP | 8-245549 | 9/1996 |
| JP | 9-110824 | 4/1997 |
| WO | WO 94/18159 | 8/1994 |
| WO | WO 94/28104 | 12/1994 |
| WO | WO 95/07883 | 3/1995 |
| WO | WO 96/16148 | 5/1996 |
| WO | WO 97/27280 | 7/1997 |
| WO | WO 99/09004 | 2/1999 |

OTHER PUBLICATIONS

"Houben Weyl: Methoden der Organischen Chemie, Bd. IV/E5", (1985), Houben–Weyl Methoden Der Organischen Chemie, George Thieme Verlag, Stuttgart, DE, pp. 223–226, p. 225, Section 1.2.4.1.1.1, "säurekatalysdiert", XP002187469.

(List continued on next page.)

*Primary Examiner*—Deborah D Carr
(74) *Attorney, Agent, or Firm*—Bernard J. Graves; Michael J. Blake (57) ABSTRACT

According to the invention, waste materials containing amido-carboxylic acid esters, which are generated during the preparation of phenyl ester salts, can be converted into amido-carboxylic acids. The recovered amido-carboxylic acid is then useful in the preparation of additional phenyl ester salt by the original preparation process or other processes known in the art. The process of the invention combines a waste material containing amido-carboxylic acid esters with an aqueous solution of a strong acid having a pH less than about 1 to form a mixture. The process heats the mixture to a temperature of at least 90° C. and maintains the mixture at that temperature for a time sufficient to hydrolyze the amido-carboxylic acid esters to amido-carboxylic acids. Sufficient base is the added to adjust the pH of the mixture to greater than about 2. The mixture is then maintained at a temperature of at least 80° C. for a time sufficient to allow phase separation of the aqueous and organic phases within the mixture. The organic phase and the aqueous phase are then separated and the amido-carboxylic acids recovered from the organic phase.

20 Claims, 6 Drawing Sheets

U.S. PATENT DOCUMENTS

| | | | |
|---|---|---|---|
| 4,681,695 A | 7/1987 | Divo | 252/94 |
| 4,852,989 A | 8/1989 | Burns et al. | 8/107 |
| 5,391,780 A | 2/1995 | Zima et al. | 554/69 |
| 5,391,783 A | 2/1995 | Colignon et al. | 554/98 |
| 5,393,901 A | 2/1995 | Zima et al. | 554/69 |
| 5,393,905 A | 2/1995 | Zima et al. | 554/70 |
| 5,414,099 A | 5/1995 | Heinzman et al. | 554/69 |
| 5,429,773 A | 7/1995 | Sherry et al. | 252/554 |
| 5,466,840 A | 11/1995 | Lutz et al. | 554/142 |
| 5,523,434 A | 6/1996 | Burns et al. | 554/68 |
| 5,534,195 A | 7/1996 | Chapman et al. | 510/444 |
| 5,534,196 A | 7/1996 | Chapman et al. | 252/186.27 |
| 5,565,590 A | 10/1996 | Zima et al. | 554/69 |
| 5,650,527 A | 7/1997 | Lutz et al. | 554/68 |
| 5,717,118 A | 2/1998 | Lutz et al. | 554/69 |

OTHER PUBLICATIONS

Database Crossfire Beilstein Online! Beilstein Institut zur Förderung der Chemischen Wissenschaften, Frankfurt am Main, DE; Database accession No. 4653647, XP002187471 abstract & Egbertson et al: Bioorganic & Medicinal Chemistry Letters, vol. 6, No. 21, (1996) pp. 2519–2524, Oxford, GB, ISSN: 0960–894X.

March J: "Advanced Organic Chemistry, Reaction, Mechanisms and Structure, 2nd Ed", Advanced Organic Chemistry, McGraw –Hill, US, p 349, section 0–11 "hydrolysis of esters", XP002187470.

SPS     C9 Amido Acid

SPS     C9 Fatty Acid

SPS     Acetic Acid

PROCESS FOR RECYCLING AMIDO-CARBOXYLIC ACID ESTERS INTO AMINO-CARBOXYLIC ACIDS

This application claims priority under 35 U.S.C. § 119 to provisional application Ser. No. 60/208,503, filed Jun. 2, 2000, which is incorporated herein by reference.

FIELD OF THE INVENTION

This invention relates to a process for recycling amido-carboxylic acid esters into amido-carboxylic acids. More particularly, the invention relates to the recycling of waste materials that are produced during the preparation of a phenyl ester salt bleach activators. These waste materials typically contain amido-carboxylic acid esters which, through the invention, may be converted into amido-carboxylic acids. These amido-carboxylic acids may then be recycled and used to prepare the phenyl ester bleach activators.

BACKGROUND

Hypochlorite and hydrogen peroxide are well known for their bleaching properties. As a bleaching agent in laundry detergents, hydrogen peroxide has the advantage of being safe to use with many fabric dyes. However, hydrogen peroxide bleaches are not effective at temperatures below 50° C. This limits their use as most laundering is carried out at temperatures below about 40° C. For this reason, various peroxyacids were developed as alternative bleaching agents for use in laundry detergents. The peroxyacids were generally found to be effective bleaching agents at the lower laundering temperatures. Because of their chemical instability and potential safety hazards, however, peroxyacids themselves are generally unsuitable for storage and handling.

Bleach activators were developed to address storage and handling concerns associated with peroxyacids. Bleach activators have the ability to hydrolyze under laundering conditions, effectively producing peroxyacids, even at lower temperatures, e.g. below 40° C. By perhydrolyzing bleach molecules, bleach activators enhance the activity, and thus the cleaning ability, of a laundry detergent. Bleach activators have the further advantage of being stable when stored in solid form at room temperature. These properties permit the use of bleach activators in a wide variety of laundry detergents and other cleaning formulations.

An important class of bleach activators is phenyl ester salts. An effective bleach activator, phenyl ester salts readily react with bleach to form the corresponding peroxyacid. Exemplary phenyl ester salts, which are used as bleach activators, are described in U.S. Pat. Nos. 4,634,551; 4,852,989; 5,391,780; 5,393,905; 5,393,901; 5,414,099; 5,466,840; 5,523,434; 5,650,527; and 5,717,118; as well as in published PCT applications WO 94/18159, WO 95/07883, WO 96/16148, and WO 99/09004. These U.S. Patents and published PCT applications are incorporated herein in their entirety.

Generally, phenyl ester salts are compounds of formula (I) or (II):

In formula (I) or (II), $R^1$ is selected from $C_1$–$C_{22}$ alkyl, $C_2$–$C_{22}$ alkenyl, $C_2$–$C_{22}$ alkynyl, $C_3$–$C_{22}$ cycloalkyl, and $C_6$–$C_{14}$ aryl. Preferably, $R^1$ is selected from $C_6$–$C_{10}$ alkyl, and $C_6$–$C_{10}$ aryl.

$R^2$ and $R^5$ are each independently selected from hydrogen, $C_1$–$C_{22}$ alkyl, $C_2$–$C_{22}$ alkenyl, $C_2$–$C_{22}$ alkynyl, $C_3$–$C_{22}$ cycloalkyl, and $C_6$–$C_{14}$ aryl. Alternatively, in formula II, $R^2$ and $R^5$, together with the nitrogen carrying them, form a $C_3$–$C_{10}$ heterocycle. This heterocycle may or may not contain additional heteroatoms selected from: nitrogen, oxygen, sulfur, or phosphorous. Preferably, $R^2$ is hydrogen, and $R^5$ is selected from hydrogen, $C_6$–$C_{10}$ alkyl, and $C_6$–$C_{10}$ aryl.

$R^3$ and $R^4$ are each independently selected in each instance from hydrogen, $C_1$–$C_{10}$ alkyl, $C_2$–$C_{10}$ alkenyl, $C_2$–$C_{10}$ alkynyl, $C_3$–$C_{10}$ cycloalkyl, and $C_6$–$C_{10}$ aryl. The $R^3$ and $R^4$ groups, together with the carbon carrying them, may form a $C_3$–$C_{10}$ cycloalkyl group. This cycloalkyl group may or may not contain heteroatoms selected from: nitrogen, oxygen, sulfur, or phosphorous. Preferably, $R^3$ and $R^4$ are independently selected in each instance from hydrogen and methyl.

The substituent Y on the phenyl ring is selected from $SO_3^-M^+$, $CO_2^-M^+$, $SO_4^-M^+$, and $N^+(R^7)_3X^-$. M represents a cation, and may be selected from hydrogen, ammonium and alkali metal atom. $R^7$ in each instance is independently a $C_1$–$C_4$ alkyl group. X is an anion, and may be selected from a halide, hydroxide, methylsulfate, or acetate ion. Preferably, Y is selected from $SO_3^-M^+$, and $CO_2^-M^+$; where M is a sodium ion.

The phenyl ring may also be further substituted with 1 to 4 other substituents. The substituents may be electron-withdrawing or electron-donating groups. The substituents may, for example, be chosen to adjust the perhydrolysis rate, to adjust the hydrophilic/hydrophobic nature of the phenyl ester salt, or to adjust the solubility of the phenyl ester salt. Possible groups include, but are not limited to, hydroxyl, halogen, $C_1$–$C_{10}$ alkyl, $C_2$–$C_{10}$ alkenyl, $C_2$–$C_{10}$ alkynyl, $C_3$–$C_{10}$ cycloalkyl, and $C_1$–$C_{10}$ alkoxy, and amino groups. When the phenyl ester salts are to be used as bleach activators, it is also desirable to have electron-withdrawing groups on the phenyl ring, to facilitate perhydrolysis or bleach activation.

The value of "m" is 0 or 1 and represents the presence or absence of an amido group in the compound. Acceptable values for "n" may range from about 0 to 20, and preferred values for "n" include from about 0 to about 6.

Phenyl ester salts can be prepared in various ways. For example, sodium nonanamidohexanoyloxybenzenesulfonate can be prepared by reacting a $C_9$ fatty acid with caprolactam to form 6-nonanoylamidohexanoic acid. Sodium p-hydroxybenzenesulfonate and acetic anhydride is then reacted with the 6-nonanoylamidohexanoic acid in a solvent to form sodium nonanamidohexanoyloxybenzenesulfonate. This reaction scheme is shown below in Scheme 1:

Notable by-products from the synthesis of phenyl ester salts include various polyamido acids (nonanamido [hexanamido]-n-hexanoic acid), sodium nonamidohexanolyloxybenzenesulfonate, and sodium nonanoyloxybenzenesulfonate. Purification of phenyl ester salts, such as by solvent crystallization, produces a waste stream containing a substantial amount of amido esters. Further waste is created when a substandard phenyl ester salt is produced and cannot be economically purified further. Although U.S. Pat. No. 5,393,901 discloses a method of maximizing recovery and recycling reactants in a process for preparing amido-carboxylic acids, it does not disclose any methods of recycling these waste materials.

Recycling such waste material into useful materials and ultimately into a purified phenyl ester salt would reduce both the waste disposal costs and costs associated with the overall preparation of phenyl ester salts and detergent formulations. Accordingly, there exists a need to recycle waste materials containing amido-carboxylic acid esters into amido-carboxylic acids that may be used to prepare phenyl ester salts.

SUMMARY OF THE INVENTION

In view of the industry's need to recycle waste materials containing amido-carboxylic acid esters waste, the invention offers valuable processes for recycling such waste. Accordingly, the invention relates to a process for recycling amido-carboxylic acid esters into amido-carboxylic acids. The process combines a waste material containing amido-carboxylic acid esters with an aqueous solution of a strong acid having a pH <about 1 to form a mixture. The process heats the mixture to a temperature and for a time sufficient to hydrolyze the amido-carboxylic acid esters to amido-carboxylic acids. Sufficient base is added to adjust the pH of the mixture to >about 2. The mixture is then maintained at a temperature below reflux for a time sufficient to allow phase separation of the liquid aqueous and organic phases within the mixture. The organic phase is then separated from the aqueous phase and the amido-carboxylic acids recovered from the organic phase.

DETAILED DESCRIPTION

According to the invention, waste materials containing amido-carboxylic acid esters, which are generated during the preparation of phenyl ester salts, can be converted into amido-carboxylic acids. The recovered amido-carboxylic acid is then useful in the preparation of additional phenyl ester salt by the original preparation process or other processes known in the art. The process combines a waste material containing amido-carboxylic acid esters with an aqueous solution of a strong acid having a pH <about 1 to form a mixture. The process heats the mixture to a temperature and for a time sufficient to hydrolyze the amido-carboxylic acid esters to amido-carboxylic acids. Sufficient base is added to adjust the pH of the mixture to >about 2. The mixture is then maintained at a temperature below reflux for a time sufficient to allow phase separation of the liquid aqueous and organic phases within the mixture. The organic phase is then separated from the aqueous phase and the amido-carboxylic acids recovered from the organic phase.

Exemplary amido-carboxylic acids to be recovered from the process of the invention can be represented by formulas III or IV:

(III)

(IV)

Figure 5:
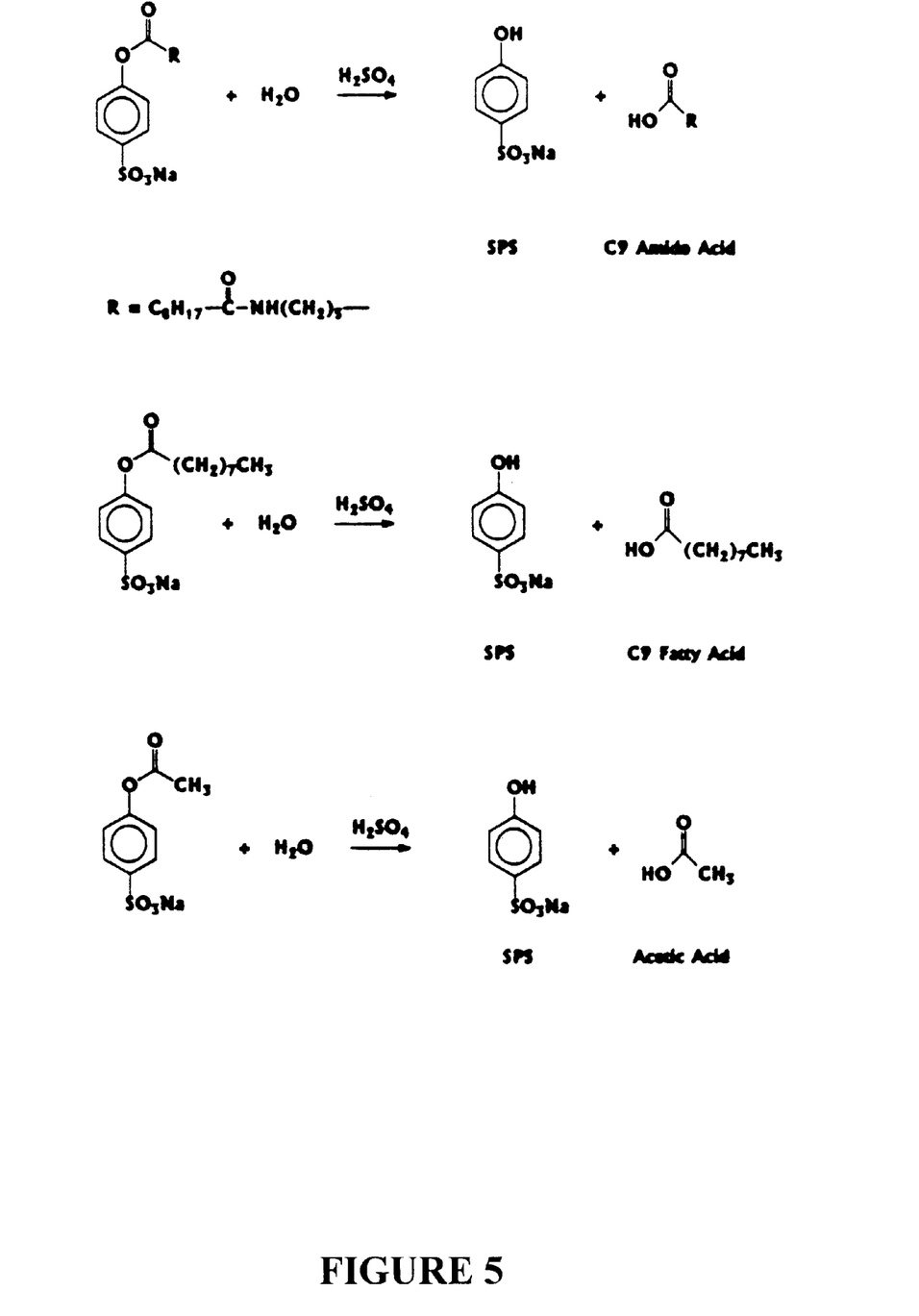
FIG. 5 depicts hydrolysis products of exemplary phenyl ester salts.

In Formulas III and IV, the substituents $R^1$, $R^2$, $R^3$, $R^4$ and $R^5$ and the integers m and n have the same definitions as discussed above with reference to phenyl ester salts of Formulas I and II. Typical hydrolysis products of some phenyl ester salts are shown in FIG. 5.

A process for recycling amido-carboxylic acid esters into amido-carboxylic acids begins with a waste material containing amido-carboxylic acid esters. The waste material may be any waste or by-product containing an amido-carboxylic acid ester. Any ester of an amido-carboxylic acid may be recycled to its corresponding amido-carboxylic acid using the process of the invention. As described above, the waste material may be by-products and/or wastes produced from the preparation or purification of phenyl ester salts, precipitates, filtrates, centrates, etc., and can include impure phenyl ester salts themselves. The waste material may be a solid or a liquid. The waste material to be processed according to the invention may contain residual solvent, typically water or other polar solvent. Preferably, the waste material contains less than about 10 wt % residual solvent, more preferably less than about 5 wt %. The waste material is preferably a solid with any volatile organic compounds removed. Volatile organic compounds, such as solvents or acetic acid used in the synthesis and purification of phenyl ester salts, may be removed by evaporation or other drying techniques known in the art. When a volatile organic such as acetic acid is present, it is preferable to remove it by evaporation. The amount of amido-carboxylic acid esters in the waste material may vary, but waste materials with significant amounts of amido-carboxylic acid esters are preferred.

As a first step to recycle the amido-carboxylic acid esters, a waste material containing amido-carboxylic acid esters is combined with an aqueous solution of a strong acid having a pH <about 1 to form a mixture. The aqueous solution is preferably water and the strong acid but may contain some organic solvents. Certainly when combined with the waste material the aqueous solution will contain organic solvents and compounds. The acid catalyzes the hydrolysis of the amido-carboxylic acid ester to its corresponding amido-carboxylic acid. Examples of suitable acids include, but are not limited to, mineral acids such as sulfuric acid, hydrochloric acid, or nitric acid, and carboxylic acids such as acetic acid and formic acid. The amount of acid used is that amount which is capable of forming an aqueous waste material solution having a pH of less than 1. Preferably, the pH ranges from about 0.5 to 0.8 and is more preferably about 0.6. To ensure good mixing, when combining the waste material with the aqueous solution, the mixture may be shaken, stirred, or agitated by other means known in the art.

To ensure hydrolysis, the mixture is heated to a temperature and for a time sufficient to hydrolyze the amido-carboxylic acid esters to amido-carboxylic acids. The temperature should be sufficient to melt any solid organic material in the waste material. The temperature may be as high as the reflux temperature of the mixture. The temperature typically ranges about 70° C. to about 100° C. Preferably, the mixture is heated to reflux. The heating step is preferably done while stirring the heated mixture. The time and temperature sufficient to effect hydrolysis of the esters in solution varies depending on the pH of the aqueous solution, the particular acid, as well as the composition of the waste material. Heating the mixture for too short a period or at too low a temperature may result in incomplete hydrolysis. Heating the ester solution for too long a period or at too high a temperature may unduly degrade the hydrolyzed esters. Refluxing the mixture at approximately 100° C. for two hours, for example, has generally been found to effect substantially complete hydrolysis without excessive degradation.

After heating the mixture to hydrolyze the amido-carboxylic acid esters, sufficient base to adjust the pH of the mixture to >about 2. The base is added to the heated mixture, although the temperature may be less than that of the heating step. Adding the base neutralizes a portion of the acid within the mixture; that is, the excess acid which catalyzes the hydrolysis reaction. If the pH is raised too high, however, neutralization (saponification) of the amido-carboxylic acid and fatty acid components can occur. Therefore, it is preferable to raise the pH to about 2 to 3.5, more preferably from about 2.5. Suitable bases include alkaline metal hydroxides, such as, for example, sodium hydroxide, potassium hydroxide, magnesium hydroxide.

After neutralization, the mixture is maintained at a temperature below reflux for a time sufficient to allow phase separation of the liquid aqueous and organic phases within the mixture. The mixture should preferably be maintained at a temperature where the organic phase remains liquid and may be heated to a temperature below the boiling point of the aqueous phase. Temperatures ranging from about 50° C. to about 90° C. are generally sufficient to allow phase separation of the aqueous and organic phases within the mixture. Phase separation may be achieved by letting the mixture remain in the reaction vessel or by transferring the heated mixture to a heated separation vessel in a manner that maintains its temperature during the transfer. The resulting aqueous and organic phases generally will have similar densities. The recycled amido-carboxylic acid is contained in the organic phase.

The organic phase and the aqueous phase may be separated by any technique known in the art. For example, the phases may be separated by decantation, centrifugation, in a separation column, etc. The mixture should be heated while the mixture separates into phases and while the phases are separated. As discussed above, the mixture may be heated to a temperature above the melting point of the organic phase and near the boiling point of the aqueous phase. Maintaining an elevated temperature generally achieves this result and aids in separating the organic phase from the salt-containing aqueous phase. Having adjusted the pH in the prior step also aids in separation. Not to be bound by theory, but adjusting pH causes acids present in the aqueous layer to form salts thereby increasing the density of the aqueous layer and improving separation.

To further aid in separation, a salt may be added to the mixture either when adding the base to adjust the pH or when allowing the mixture to separate into an aqueous and organic phase. The salt is added in an amount sufficient to increase phase separation and to avoid emulsion formation. Generally, the salt concentration can be from about 1 wt % up to saturation of the aqueous phase. Preferably the salt concentration is about 5 wt % or less, more preferably about 3 wt % or less. The presence of salt in excess of saturation is permissible so long as it does not interfere with separation. The selection of a salt as a separation aid is not critical. Any salts commonly used in the industry, such as alkaline sulphates, chlorides, nitrates, etc., is adequate. Exemplary salts, such as, sodium sulphate, potassium sulphate, magnesium sulphate, sodium chloride, potassium chloride, magnesium chloride, sodium nitrate, potassium nitrate, etc. may be used. It is preferable, however, to use a salt corresponding to the salt product of the neutralization of the acid by the base added when adjusting the pH of the mixture.

Having separated the organic phase from the aqueous phase, the amido-carboxylic acids are then recovered from the organic phase. The amido-carboxylic acids may be recovered by removing any volatile organic compounds or solvents. The recovered amido-carboxylic acids generally are in the form of an oil or a raffinate. The amido-carboxylic acids may be purified by drying the organic phase before recovering the amido-carboxylic acids, by distillation, by washing, or by re-crystallization. The recovered amido-carboxylic acids may then be recycled for use in chemical processes, such as the preparation of phenyl ester salts.

As can be understood, from the discussion of the above steps with their preferred embodiments, the invention also relates to an overall process for recycling amido-carboxylic acid esters into amido-carboxylic acids according to the invention. This overall preferred process comprises the steps of:

(a) removing any volatile materials from the waste material containing the amido-carboxylic acid esters, (b) combining a waste material containing amido-carboxylic acid esters with an aqueous solution of a strong acid having a pH <about 1 to form a mixture, (c) heating the mixture to a temperature and for a time sufficient to hydrolyze the amido-carboxylic acid esters to amido-carboxylic acids, (d) adding sufficient base to adjust the pH of the mixture to >about 2, (e) adding a salt to the mixture, wherein the salt is added in an amount sufficient to increase phase separation and to avoid emulsion formation, (f) maintaining the mixture at a temperature below reflux for a time sufficient to allow phase separation of the aqueous and organic phases within the mixture, (g) separating the organic phase and the aqueous phase, and (h) recovering the amido-carboxylic acids from the organic phase.

The preferred embodiments for this overall process are the same as those discussed above. The overall process may also contain the additional steps discussed above.

Figure 1:
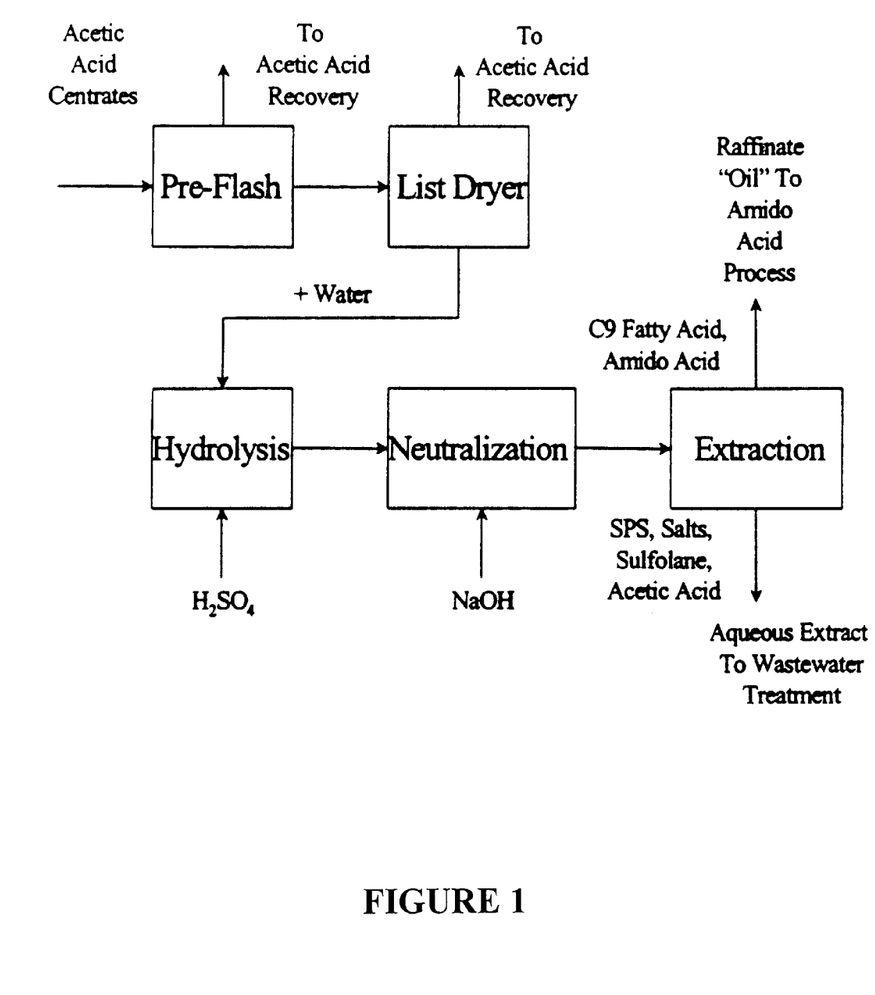
FIG. 1 is a schematic drawing of a preferred sequence of unit operations in a sodium nonanamidohexanoyloxybenzenesulfonate hydrolysis process.

The processes of the invention may be performed as a batch process, a semi-batch process or a continuous process. In a preferred embodiment, an amido-carboxylic acid is continuously recovered from an amido-carboxylic acid ester waste stream and recycled. FIG. 1 shows a particularly preferred sequence of unit operations with typical solvents and reactants. In this embodiment, acetic acid centrates from sodium nonanamidohexanoyloxybenzenesulfonate isolation, which contain amido esters, are concentrated in an initial pre-flash step. Using methods known in the art, such as vacuum and heat, the waste is concentrated to about a 50% solids slurry. Most or all of the solvent in the slurry may then be removed using a suitable dryer. Preferred dryers are mechanically agitated driers capable of handling viscous material such as a Porcupine dryer from Bethlehem Corporation, Easton, Pa., or a List dryer, from List Corporation, Acton, Mass. The dried solids are mixed with water and an acid catalyst, such as sulfuric acid, to hydrolyze the amido esters into amido-carboxylic acids. The hydrolyzed product is then neutralized with sodium hydroxide. Lastly, the organic layer, which contains the amido-carboxylic acid product, is separated from the aqueous layer and recycled. Phenolic impurities, such as sodium acetyloxybenzenesulfonate (ABS) and sodium phenolsulfonate (SPS), and any residual solvents are present in the water layer and sent to a wastewater treatment facility.

The following examples are intended to illustrate, but not limit, the scope of the present invention. The waste materials used were those generated in the preparation of the phenyl ester salt, sodium 4-sulfophenyl-6-[(1-oxynonyl)-amino] hexanoate, prepared from the reaction of sodium 4-hydroxybenzenesulfonate, acetic anhydride, and nonanamidohexanoic acid in sulfolane with sodium acetate, imidazole, and/or caustic as catalysts(s), as described in U.S. Pat. No. 5,650,527.

In the Examples below, the following numbers and acronyms identify the following compounds:

| | |
|---|---|
| (1) | Nonanamidohexanoic acid |
| (2) | Nonanamidohexanamidohexanoic acid |
| (3) | Sodium nonanamidohexanoyloxybenzenesulfonate |
| (4) | Sodium nonanamidohexanamidohexanoyloxybenzenesulfonate |
| (5) | 2-methyloctanamidohexanoic acid |
| (6) | 2-methyloctanamidohexanamidoheaxanoic acid |
| (7) | Sodium 2-methyloctanamidohexanoyloxybenzenesulfonate |
| (8) | Sodium nonanoyloxybenzenesulfonate |
| (9) | 2-methyloctanamidohexanoic acid |
| ABS | Sodium acetyloxybenzenesulfonate |
| SPS | Sodium phenolsulfonate |

EXAMPLE 1

Batch Recovery of Amido-carboxylic Acid 500 g ester waste (a filtrate from a process such as described in Example 4 of U.S. Pat. No. 5,466,840) was added to a solution of 66 g concentrated sulfuric acid dissolved in approximately 1200 g water. The mixture was placed in a 2-liter 3-neck round bottom flask fitted with a reflux condenser, a heating mantle, and a magnetic stirrer and heated for two hours at reflux (ca. 100° C.). A 50% sodium hydroxide solution was then added through the condenser to adjust the pH to 2.5. After hot transfer of the resulting solution to a separatory funnel, phase separation occurred after standing for approximately 5 minutes at 80° C. The salt-containing aqueous layer (1490 g) was drawn off the bottom, leaving 330 g of organic product. Table 1 shows the composition of the organic layer, aqueous layer, and the ester waste.

TABLE I

| | Ester waste (wt. %) | Water layer (wt. %) | Organic (product) layer (wt. %) |
|---|---|---|---|
| (3) | 53.0 | ND | ND |
| (4) | 8.6 | ND | 2.0 |
| (1) | 4.8 | ND | 44.7 |
| (2) | 2.3 | ND | 7.9 |
| SPS | 12.2 | 14.5 | 3.8 |

Figure 2:
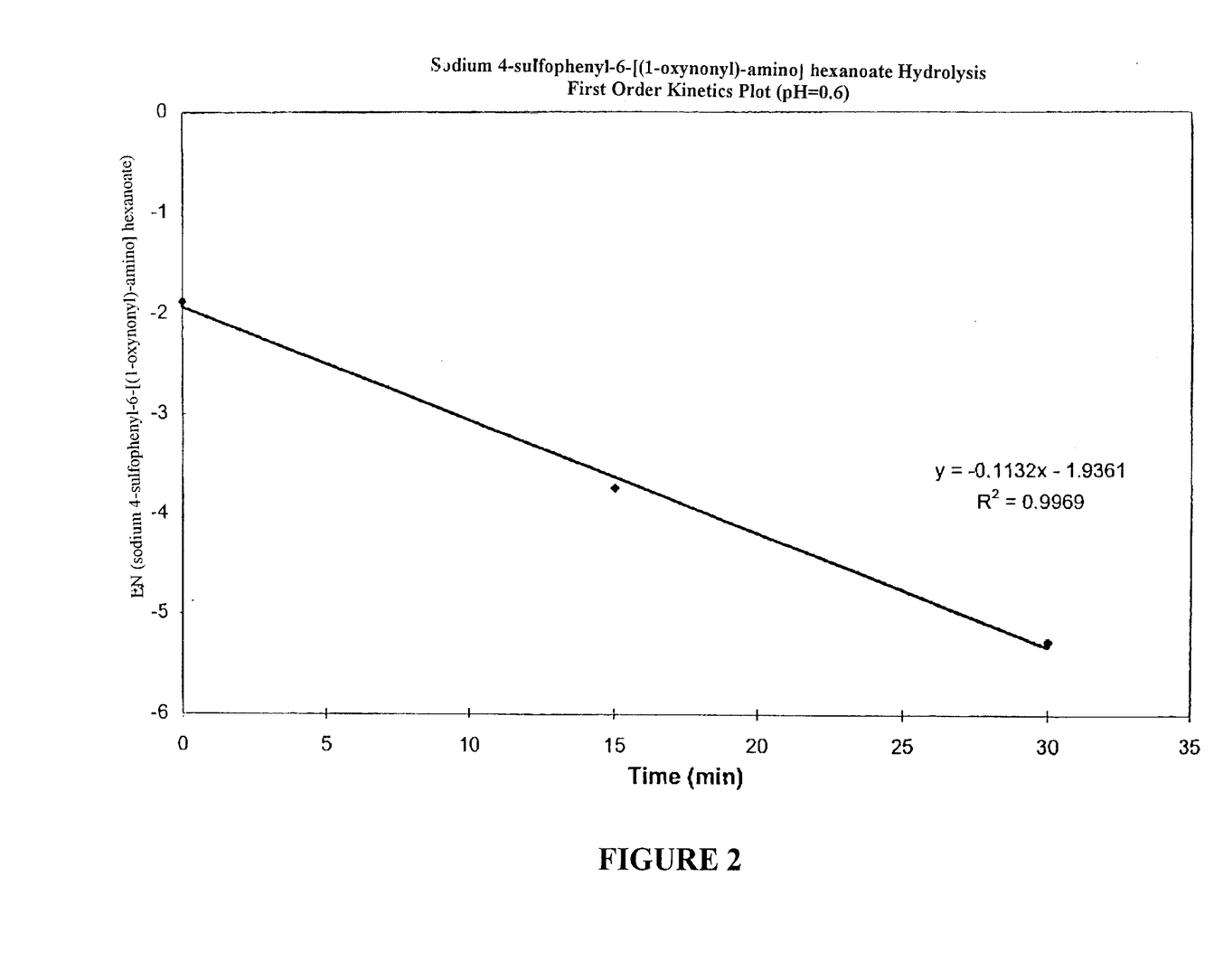
FIG. 2 is a first order kinetics plot for the hydrolysis of sodium nonanamidohexanoyloxybenzenesulfonate at pH 0.6.
Figure 3:
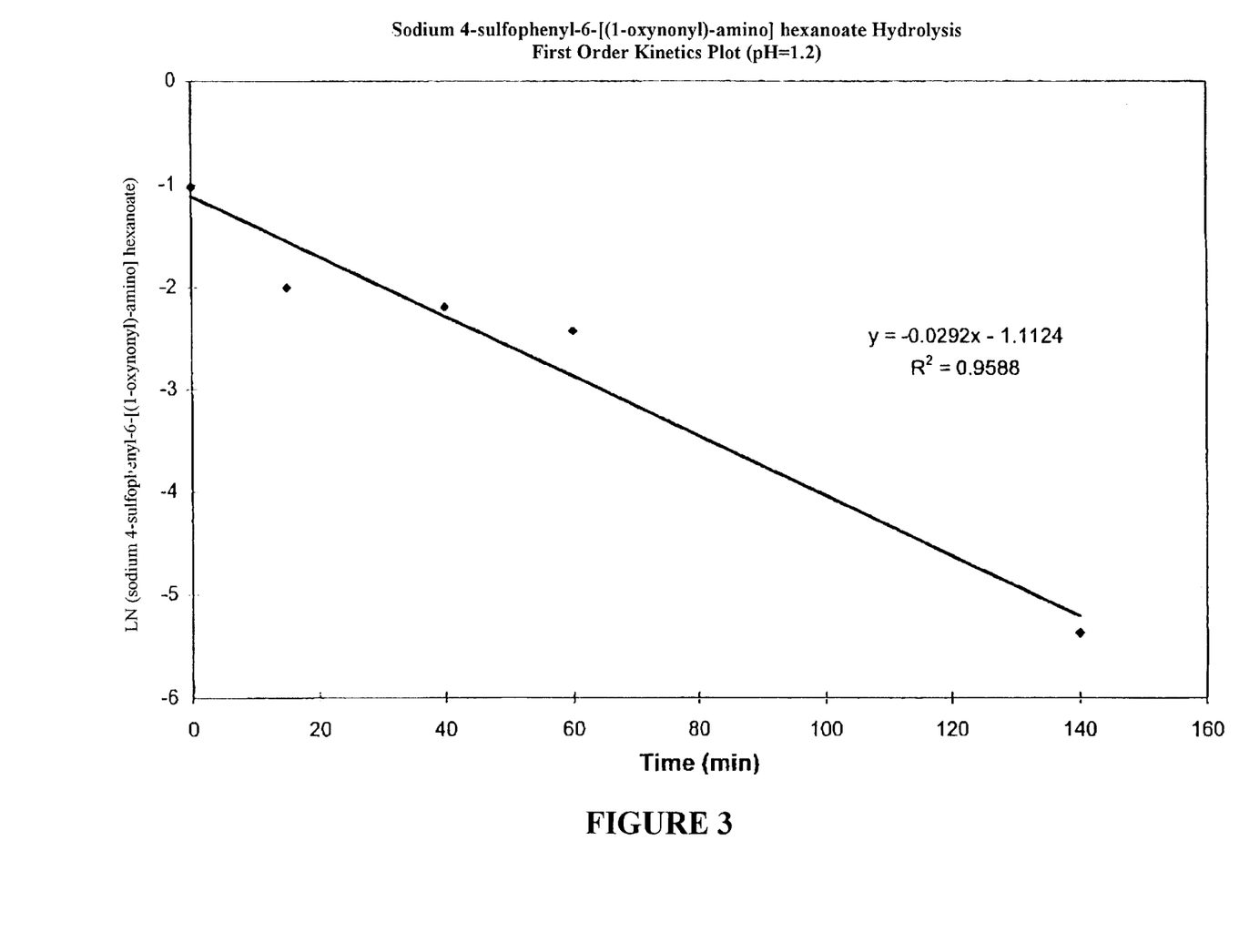
FIG. 3 is a first order kinetics plot for the hydrolysis of sodium nonanamidohexanoyloxybenzenesulfonate at pH 1.2.

The pH of hydrolysis was measured to be 0.6. FIG. 2 shows a change in the concentration of sodium nonanamidohexanoyloxybenzenesulfonate as a function of time at pH 0.6. Based on this graph, the first order rate constant was estimated to be 0.1132 min$^{-1}$. In another similar experiment, a kinetics plot for the hydrolysis of sodium nonanamidohexanoyloxybenzenesulfonate, shown in FIG. 3, was determined at a pH of 1.2. The first order rate constant for this process was about 0.0292 min$^{-1}$.

EXAMPLE 2

Continuous Recovery of Amido-carboxylic Acid with Decanter

Figure 6:
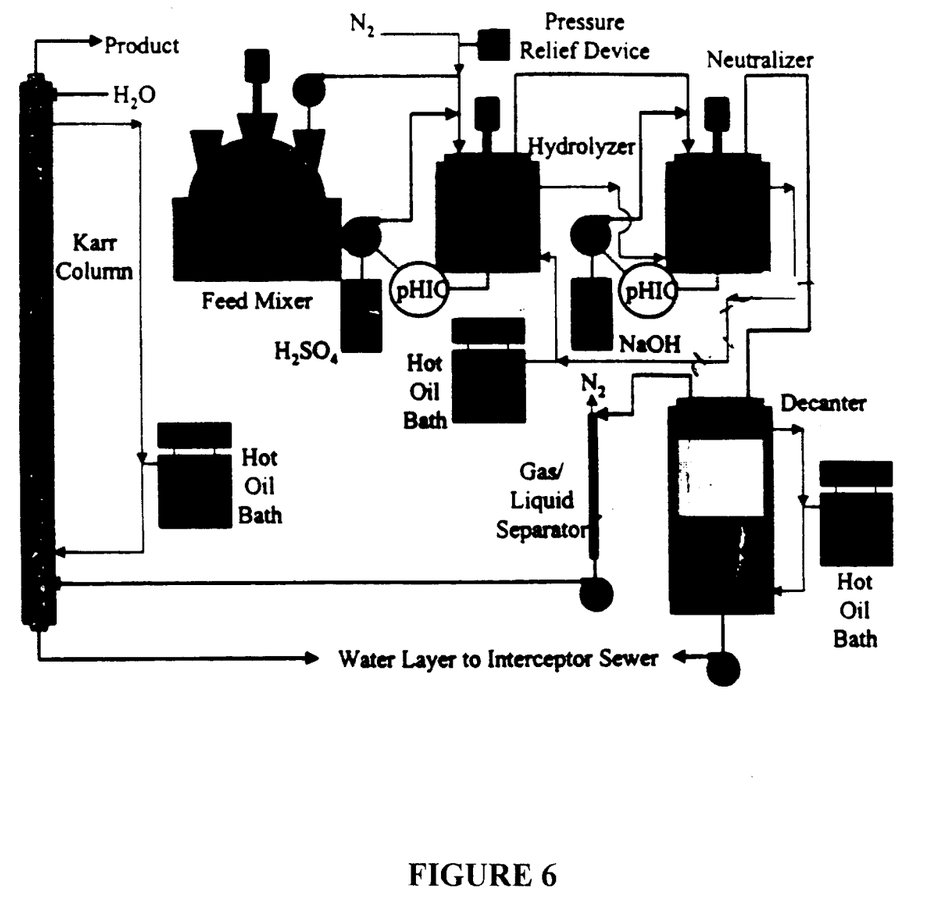
FIG. 6 depicts a schematic diagram for the hydrolysis of sodium nonanamidohexanoyloxybenzenesulfonate on a bench-scale pilot plant.

The continuous process was conducted using a glass 22-liter feed mixer, a glass 1.5-liter hydrolysis vessel, a glass 1.0-liter neutralization vessel, a glass 4.0-liter decanter, and a glass ½-inch diameter Karr extraction column. See FIG. 6. Continuous transfer of materials between vessels was accomplished primarily through the use of metering pumps and nitrogen-induced pressure gradients. A series of three hot oil recirculating baths was used to control temperature in the reaction vessels, decanter, and Karr column. Temperature control in the 316SS transfer tubing was accomplished with single loop PID controllers and electrical heating tape.

Waste material, consisting primarily of centrates, was obtained during the preparation of sodium nonanamidohexanoyloxybenzenesulfonate. Some acetic acid was removed during a pre-flash step to produce waste material containing about 50 wt % acetic acid. Acetic acid was further removed using a List model DTB-3 Batch Dryer, List Co. (Acton, Mass.).

Weighed portions of the dried sodium nonanamidohexanoyloxybenzenesulfonate isolation centrates were periodically dissolved into an equal weight of 70° C. demineralized water, charged to the feed mixer, and pumped into the hydrolyzer. The pH in the hydrolyzer was controlled to a typical value of 0.6±0.1 through the use of a pH probe and controller arrangement that periodically prompted a metering pump to feed fuming (99+%) $H_2SO_4$ into the vessel. Liquid level in the hydrolyzer was maintained using a sip tube located in the head of the vessel. As the liquid level reached the mouth of the sip tube, a small flow of nitrogen forced the liquid out of the hydrolyzer through the transfer tubing and into the neutralizer. Liquid level and pH control in the neutralizer were accomplished in a similar manner except that 50% caustic was employed to raise the pH to 2.5±0.2.

Products from the neutralization vessel flowed into a decanter. The level of the interface was controlled by a thermal conductivity level probe coupled with a Yokogawa single loop PID controller. The output of the PID controller operated an FMI metering pump located at the bottom of the decanter. The level at the top of the decanter was maintained by the same type of sip tube arrangement described above. Product oil passing through the sip tube next entered the gas/liquid separator where it was disengaged from the nitrogen carrier gas.

Finally, the liquid contents of the gas/liquid separator were continuously pumped into the bottom of the glass Karr extraction column. The extraction solvent, consisting of demineralized water and $Na_2SO_4$, was pumped from a 1-gallon plastic jug into the top of the column with an metering pump. The aqueous extract was withdrawn from the bottom of the column using another metering pump. The output of this pump was manually adjusted to maintain the desired position of the oil/water interface at the top of the column. The oily raffinate product was allowed to overflow from the top of the column into a heated transfer tube that emptied into a 1-gallon plastic jug.

Weighed samples were periodically taken from the waste feed stream, the decanter overflow, the decanter underflow, the Karr column overflow, and the Karr column underflow. These samples were submitted for gas chromatography (GC) and liquid chromatography (LC) analyses. On a less frequent basis, samples were submitted to determine the amount of sodium by inductively coupled plasma emission spectroscopy (ICP) and to determine viscosity. Flow rates and densities of the various process streams were determined by accumulating the material in a pre-weighed graduated cylinder over a set period of time, typically 30 minutes, then recording the volume and mass of the contents.

The waste feed material had a density of 1.09 g/ml at 80° C. The waste was fed at a rate of 4.42 g/min to the hydrolysis reactor. The material had a residence time of 3.77 h in the hydrolysis reactor at a temperature of 90° C. and a pH of 0.6. The material was then fed to the neutralization vessel at 90° C., pH 2.5, and then to the decanter. The decanter underflow rate was 2.71 g/min and the material had a density of 1.15 g/ml at 90° C. From the decanter, the material, having a density of 1.04 g/ml, went to the Karr column at a feed rate of 2.04 g/min where the temperature was maintained at 80° C. Water containing 5 wt % sodium sulfate was fed into the top of the column at 2.09 g/min. The raffinate rate was 2.10 g/min with a density of 1.03 g/ml. The extract rate was 2.03 g/min with a density of 1.05 g/ml.

The results are summarized below in Tables II which compares the flow rate, density, and composition data for certain feed and product streams.

TABLE II

|  | Feed Composition (wt. %) | Decanter Underflow (wt. %) | Karr Feed Composition (wt. %) | Extract Composition (wt. %) | Raffinate Composition (wt. %) |
|---|---|---|---|---|---|
| (1) | 6.87 | 0 | 27.58 | 0 | 25.27 |
| (2) | 6.21 | 0 | 10.92 | 0 | 10.08 |
| (3) | 12.36 | 0.05 | 5.97 | 0 | 2.58 |
| (4) | 2.14 | 0 | 1.04 | 0 | 0.34 |
| (5) | 5.83 | 0 | 3.1 | 0 | 2.7 |
| (7) | 1.49 | 0 | 0.74 | 0 | 0.28 |
| Nonanoic acid | 1.49 | 0.02 | 5.94 | 0 | 5.26 |
| (8) | 2.33 | 0 | 1.23 | 0 | 0.77 |
| Caprolactam | 0.5 | 0.26 | 0.61 | 0.21 | 0.33 |
| HOAc | 1.96 | 2.08 | 1.64 | 1.3 | 0 |
| ABS | 1.57 | 0.25 | 0.22 | 0 | 0 |
| SPS | 5.22 | 9.62 | 4.21 | 4.35 | 1.14 |
| Sulfolane | 2.19 | 2.25 | 1.74 | 1.34 | 0.37 |
| Total | 50.16 | 14.53 | 64.94 | 7.2 | 49.12 |
| $H_2O$ (by difference) | 49.84 | 85 | 35 | 93 | 51 |

In the experiment, the conversion of sodium nonanamidohexanoyloxybenzenesulfonate in the hydrolysis reactor was unexpectedly low. Calculations based on batch hydrolysis experiments showed that at 0.6 pH and a residence time of 3.77 h, greater than 95% of the sodium nonanamidohexanoyloxybenzenesulfonate should have been hydrolyzed. Instead, only about 77% was hydrolyzed, as determined by liquid chromatographic analysis of the aqueous phase. Therefore, the apparent first-order reaction rate constant for sodium nonanamidohexanoyloxybenzenesulfonate (3) was only about 0.015 min$^{-1}$ compared to 0.1132 min$^{-1}$ for the batch experiments. Accordingly, it appears that even though the measured pH of 0.6 was the same as was used in the batch experiments, the actual concentration of sulfuric acid in the process stream was a factor of about 5–6 times lower in the continuous experiment than was the case in the batch experiment.

The following data was calculated:

| | |
|---|---|
| CSTR Performance Equation: | $X_{(3)} = \dfrac{k_{(3)}}{(k_{(3)} + 1)}$ |
| Rearranged CSTR Performance Equation: | $k_{(3)} = -\dfrac{1}{1-X_{(3)}} X_{(3)}$ |
| Mean Hydrolysis CSTR Residence Time: | = 3.77 hr |
| Predicted conversion based on batch data: | $X_{(3)} = 0.962$ |
| Actual conversion in continuous reactor: | $X_{(3)} = 0.7746$ |
| Apparent first order reaction rate constant from continuous data | $k_{(3)} = 0.015\ \text{min}^{-1}$ |
| Measured reaction rate constant at 0.6 pH based on batch data: | $k_{(3)} = 0.1132\ \text{min}^{-1}$ |

EXAMPLE 3A

Continuous Process without Decanter

In this example, the decanter was bypassed and the neutralizer product was fed directly into the gas/liquid separator. Otherwise, this example is similar to Example 2 except for the following modifications. In Example 2 a large amount of water (50 wt %) was entrained in the oily product of the Karr column. Therefore, to further the separation of the water and oil layers, an additional centrifugation step was implemented.

EXAMPLE 3B

Continuous Process without Decanter

In this continuous process example, adding 5 wt % of $Na_2SO_4$ to the water feed to the Karr column in Example 3A achieved phase separation at the top of the column. Any lesser amount resulted in the formation of an emulsion due to the low density difference and interfacial tension between the aqueous and organic phases.

EXAMPLE 3C

Continuous Process without Decanter

Further, the feed rate was cut by a factor of about 2. This caused an increase in the residence time in the hydrolysis reactor and a corresponding increase in sodium nonanamidohexanoyloxybenzenesulfonate conversion to about 94%. However, like Example 2, this is a lower conversion than would be expected based on the kinetics derived from the batch hydrolysis experiments. The apparent first order rate constant for Example 3 was calculated to be 0.035 min$^{-1}$, compared to the value of 0.1132 min$^{-1}$ for the batch experiments. As in Example 2, it appears that there was a relatively low concentration of sulfuric acid in the continuous run as compared to the batch runs.

Another important outcome was that the concentrations of acetic acid and sulfolane in the Karr column "oil" product or raffinate were both higher than desired. Part of the reason for this is that the removal of the decanter resulted in one less equilibrium stage being available to effect the separation. On the other hand, the removal of the decanter somewhat improved the operability of the Karr column because more salts were carried into the column with the process stream and were available to enhance the density difference and interfacial tension between the organic and aqueous phases. Therefore, in these continuous process examples the minimum concentration of $Na_2SO_4$ required in the water feed to the column was reduced from 5 wt % to 3 wt %.

As in Example 2, the amount of water entrained in the Karr column raffinate was excessively high (43%). To remove excess water, a portion of representative product material from Example 2 was centrifuged at 2300 g for 10 minutes at 4 different temperatures. The results are summarized in Table III. It can be seen from the data that most of the entrained water can be effectively removed by centrifugation except for the about 6–7% that is soluble in the oil phase. Distribution coefficients for all major components between the aqueous and organic phases are also tabulated.

TABLE III

| Sample | Phase | Temperature (° C.) | Phase (ml) | Aqueous Phase | Caprolactam (wt. %) | SPS (wt. %) | ABS (wt. %) | (1) (wt. %) | (2) (wt. %) | (3) (wt. %) | (4) (wt. %) | (7) (wt. %) |
|---|---|---|---|---|---|---|---|---|---|---|---|---|
| 1 | Top phase | 86 | 7 | No | 0.35 | 0.43 | 0.00 | 41.58 | 14.88 | 1.36 | 0.24 | 0.11 |
|  | Bottom phase |  | 2 | Yes | 0.10 | 9.99 | 0.00 | 0.12 | 0.00 | 0.00 | 0.00 | 0.00 |
|  | Distribution Coefficient (Aqueous/organic) | 86 |  |  | 0.29 | 23.93 |  | 0.00 | 0.00 | 0.00 | 0.00 | 0.00 |
| 2 | Top phase | 77 | 7 | No | 0.36 | 0.40 | 0.00 | 43.95 | 15.90 | 1.41 | 0.26 | 0.14 |
|  | Bottom phase |  | 2 | Yes | 0.09 | 9.91 | 0.00 | 0.00 | 0.00 | 0.00 | 0.00 | 0.00 |
|  | Distribution Coefficient (Aqueous/Organic) | 77 |  |  | 0.25 | 24.78 |  | 0.00 | 0.00 | 0.00 | 0.00 | 0.00 |
| 3 | Top phase | 80 | 7 | No | 0.35 | 0.41 | 0.00 | 42.19 | 15.35 | 1.30 | 0.27 | 0.14 |
|  | Bottom phase |  | 2 | Yes | 0.10 | 9.74 | 0.00 | 0.14 | 0.00 | 0.00 | 0.00 | 0.00 |
|  | Distribution Coefficient | 70 |  |  | 0.29 | 23.76 |  | 0.00 | 0.00 | 0.00 | 0.00 | 0.00 |

TABLE III-continued

| | (Aqueous/Organic) | | | | | | | | | | |
|---|---|---|---|---|---|---|---|---|---|---|---|
| 4 | Top phase | 60 | 7 | No | 0.31 | 1.51 | 0.00 | 35.78 | 13.38 | 1.01 | 0.20 | 0.10 |
| | Bottom phase | | 2 | Yes | 0.10 | 9.65 | 0.00 | 0.59 | 0.00 | 0.00 | 0.00 | 0.00 |
| | Distribution Coefficient (Aqueous/Organic) | 60 | | | 0.32 | 5.34 | | 0.02 | 0.00 | 0.00 | 0.00 | 0.00 |

| Sample | Phase | (8) (wt. %) | (9) (wt. %) | Water (wt. %) | Acetic Acid (wt. %) | Nonanoic Acid (wt. %) | Sulfolane (wt. %) | Analytical Accountability (wt. %) |
|---|---|---|---|---|---|---|---|---|
| 1 | Top phase | 0.32 | 4.56 | 6.62 | 0.40 | 10.70 | 0.66 | 82.73 |
| | Bottom phase | 0.00 | 0.00 | 76.71 | 0.76 | 0.40 | 0.96 | 89.06 |
| | Distribution Coefficient (Aqueous/Organic) | 0.00 | 0.00 | 11.25 | 1.90 | 0.04 | 1.48 | |
| 2 | Top phase | 0.33 | 4.30 | 7.24 | 0.40 | 10.87 | 0.66 | 86.72 |
| | Bottom phase | 0.00 | 0.00 | 76.26 | 0.75 | 0.05 | 0.93 | 88.04 |
| | Distribution Coefficient (Aqueous/Organic) | 0.00 | 0.00 | 10.53 | 1.66 | 0.00 | 1.48 | |
| 3 | Top phase | 0.25 | 4.21 | 6.60 | 0.39 | 10.43 | 0.62 | 82.51 |
| | Bottom phase | 0.00 | 0.00 | 76.98 | 0.77 | 0.03 | 1.06 | 88.62 |
| | Distribution Coefficient (Aqueous/Organic) | 0.00 | 0.00 | 11.66 | 1.97 | 0.00 | 1.71 | |
| 4 | Top phase | 0.19 | 3 73 | 7.29 | 0.40 | 10.26 | 0.63 | 76.09 |
| | Bottom phase | 0.00 | 0.00 | 76.01 | 0.77 | 0.02 | 1.08 | 88.23 |
| | Distribution Coefficient (Aqueous/Organic) | 0.00 | 0.00 | 10.43 | 1.93 | 0.00 | 1.71 | |

EXAMPLE 4

Neutralization

Figure 4:
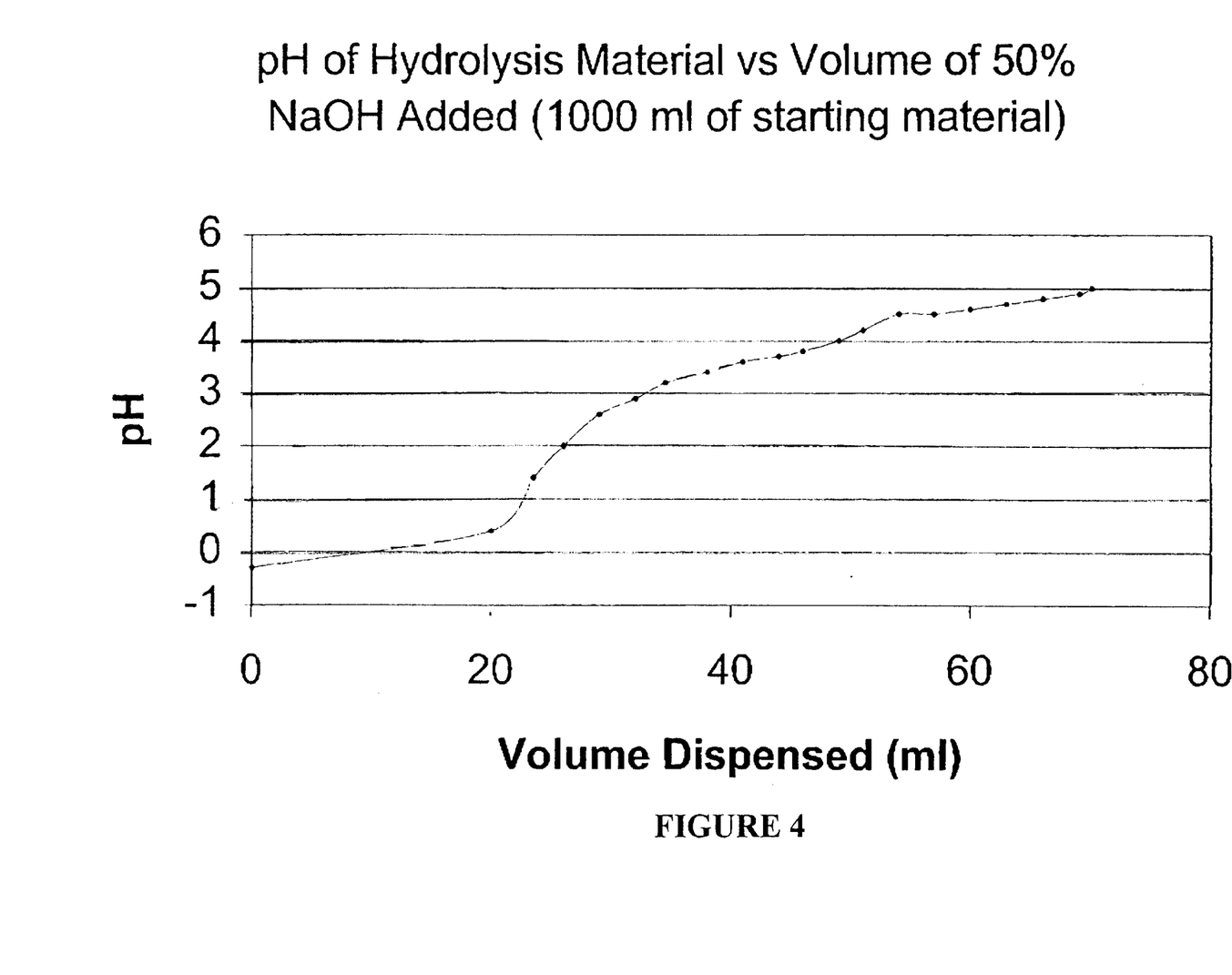
FIG. 4 is a plot of the pH of hydrolyzed material as a function of volume 50% NaOH added to 1000 mL of starting material.

At the end of Example 3, sulfuric acid was added to the contents of the hydrolyzer to reduce the pH to below zero. 50% caustic was then slowly added and the pH recorded. The curve shown as FIG. 4 was generated for pH as a function of the volume of 50% caustic added. The curve shows a relatively flat region from about pH 0 to about 0.5. Then there is a sharp rise from 0.5 up to about 2.5 where the slope begins to level off again. The sharp rise portion of the curve is the region where the neutralization of the first proton of the $H_2SO_4$ occurs, forming $NaHSO_4$. This is the desired operating region for the neutralizer because at a pH above 2.5, neutralization (saponification) of the amido acid and fatty acid components can occur. Based on the curve (shown as FIG. 4), the preferred operating pH for the neutralizer is about 2.

In summary, based on Examples 3 and 4, the following data were obtained:

| | |
|---|---|
| Hydrolysis CSTR Residence Time | = 7.81 hr |
| Predicted conversion based on batch data $X_{(3)}$ | = 0.981 |
| Actual conversion in continuous reactor $X_{(3)}$ | = 0.9428 |
| Apparent first order reaction rate constant from continuous data $k_{(3)}$ | = 0.035 min$^{-1}$ |
| Measured reaction rate constant at 0.6 pH based on batch data $k_{(3)}$ | = 0.1132 min$^{-1}$ |

The claimed invention is:

1. A process for recycling amido-carboxylic acid esters into amido-carboxylic acids comprising the steps of:
   (a) combining a waste material containing amido-carboxylic acid esters with an aqueous solution of a strong acid having a pH less than about 1 to form a mixture,
   (b) heating the mixture to a temperature and for a time sufficient to hydrolyze the amido-carboxylic acid esters to amido-carboxylic acids,
   (c) adding sufficient base to adjust the pH of the mixture to greater than about 2,
   (d) maintaining the mixture at a temperature below reflux for a time sufficient to allow phase separation of the liquid aqueous and organic phases within the mixture,
   (e) separating the organic phase and the aqueous phase, and
   (f) recovering the amido-carboxylic acids from the organic phase.

2. A process of claim 1, further comprising, after step (c), the step of adding a salt to the mixture, wherein the salt is added in an amount sufficient to increase phase separation and to avoid emulsion formation.

3. A process of claim 1, further comprising, before step (a), the step of removing any volatile materials from the waste material containing the amido-carboxylic acid esters.

4. A process of claim 1, wherein the strong acid in step (a) is sulfuric acid, hydrochloric acid, nitric acid, acetic acid, or formic acid.

5. A process of claim 1, wherein the base in step (c) is an alkaline metal hydroxide.

6. A process of claim 2, wherein the salt is an alkaline metal sulfate, an alkaline metal chloride, or an alkaline metal nitrate.

7. A process of claim 1, further comprising the step of purifying the recovered amido-carboxylic acid by distillation or recrystallization.

8. A process of claim 1, wherein the separation step (e) comprises decantation or centrifugation.

9. A process of claim 1, wherein step (b) refluxes the mixture for a time sufficient to hydrolyze the amido-carboxylic acid esters to amido-carboxylic acids.

10. A process of claim 9, further comprising, before step (a), the step of removing any volatile materials from the waste material containing the amido-carboxylic acid esters.

11. A process of claim 9, further comprising, after step (c), the step of adding a salt to the mixture, wherein the salt is added in an amount sufficient to increase phase separation and to avoid emulsion formation.

12. A process of claim 9, wherein the strong acid in step (a) is sulfuric acid, hydrochloric acid, nitric acid, acetic acid, or formic acid.

13. A process of claim 9, wherein the base in step (c) is an alkaline metal hydroxide.

14. A process of claim 11, wherein the salt is an alkaline metal sulfate, an alkaline metal chloride, or an alkaline metal nitrate.

15. A process of claim 9, further comprising the step of purifying the recovered amido-carboxylic acid by distillation or recrystallization.

16. A process for recycling amido-carboxylic acid esters into amido-carboxylic acids comprising the steps of:

(a) removing any volatile materials from the waste material containing the amido-carboxylic acid esters, (b) combining a waste material containing amido-carboxylic acid esters with an aqueous solution of a strong acid having a pH less than about 1 to form a mixture, (c) heating the mixture to a temperature and for a time sufficient to hydrolyze the amido-carboxylic acid esters to amido-carboxylic acids, (d) adding sufficient base to adjust the pH of the mixture to greater than about 2, (e) adding a salt to the mixture, wherein the salt is added in an amount sufficient to increase phase separation and to avoid emulsion formation, (f) maintaining the mixture at a temperature below reflux for a time sufficient to allow phase separation of the aqueous and organic phases within the mixture, (g) separating the organic phase and the aqueous phase, and (h) recovering the amido-carboxylic acids from the organic phase.

17. A process of claim 16, wherein step (c) refluxes the mixture for a time sufficient to hydrolyze the amido-carboxylic acid esters to amido-carboxylic acids.

18. A process of claim 16, further comprising, before step (a), the step of removing any volatile materials from the waste material containing the amido-carboxylic acid esters.

19. A process of claim 16, wherein: the strong acid in step (b) is sulfuric acid, hydrochloric acid, nitric acid, acetic acid or formic acid; the base in step (d) is an alkaline metal hydroxide; and the salt in step (e) is an alkaline metal sulfate, an alkaline metal chloride, or an alkaline metal nitrate.

20. A process of claim 16, wherein the separation step (g) comprises decantation or centrifugation and further comprising the step (i) of purifying the recovered amido-carboxylic acid by distillation or recrystallization.

* * * * *